(12) United States Patent
Thompson et al.

(10) Patent No.: US 10,429,278 B2
(45) Date of Patent: Oct. 1, 2019

(54) COMPOSITE GAS SAMPLING SYSTEM

(71) Applicant: Mustang Sampling, LLC, Ravenswood, WV (US)

(72) Inventors: Kenneth O. Thompson, Ravenswood, WV (US); Claude A. Rolston, St. Marys, WV (US); Timothy Layne Querrey, Murraysville, WV (US)

(73) Assignee: Mustang Sampling, LLC, Ravenswood, WV (US)

( * ) Notice: Subject to any disclaimer, the term of this patent is extended or adjusted under 35 U.S.C. 154(b) by 319 days.

(21) Appl. No.: 15/355,776

(22) Filed: Nov. 18, 2016

(65) Prior Publication Data
US 2017/0067802 A1    Mar. 9, 2017

Related U.S. Application Data

(62) Division of application No. 14/205,526, filed on Mar. 12, 2014, now Pat. No. 9,562,833.
(Continued)

(51) Int. Cl.
*G01N 1/26* (2006.01)
*G01N 1/18* (2006.01)
(Continued)

(52) U.S. Cl.
CPC ............ *G01N 1/2247* (2013.01); *G01N 1/18* (2013.01); *G01N 1/26* (2013.01); *G01N 30/88* (2013.01); *G01N 33/0014* (2013.01); *G01N 33/0016* (2013.01); *G01N 33/0047* (2013.01); *G01N 33/0073* (2013.01); *G01N 2001/105* (2013.01); *G01N 2001/1093* (2013.01); *G01N 2001/2071* (2013.01); *G01N 2001/2261* (2013.01);
(Continued)

(58) Field of Classification Search
CPC .......... G01N 1/2247; G01N 1/18; G01N 1/26
USPC ....................................................... 73/863
See application file for complete search history.

(56) References Cited

U.S. PATENT DOCUMENTS

| | | |
|---|---|---|
| 653,931 A | 7/1900 | Lowres |
| 3,681,997 A | 8/1972 | Allen |

(Continued)

FOREIGN PATENT DOCUMENTS

| | | |
|---|---|---|
| CN | 1482444 A | 3/2004 |
| CN | 101228424 A | 7/2008 |

(Continued)

OTHER PUBLICATIONS

International Application No. PCT/US14/027787, International Search Report, dated Jul. 24, 2014.
(Continued)

*Primary Examiner* — John Fitzgerald
*Assistant Examiner* — Rodney T Frank
(74) *Attorney, Agent, or Firm* — Cahn & Samuels, LLP

(57) ABSTRACT

A sampling system for collecting periodic composite and/or non-composite samples of vaporized gas during a transfer process from a vaporizer of a cryogenic hydrocarbon liquid including 1) a direct sample pathway to a gas analyzer for instantaneous, real-time vaporized gas analysis, 2) a speed loop pathway for directly collecting fresh vaporized gas samples for subsequent analysis, and 3) a composite sample pathway including a pressurized sample accumulator for collecting a plurality periodically obtained samples of a select volume during the transfer process to create a composite sample of the vaporized gas.

6 Claims, 4 Drawing Sheets

Related U.S. Application Data

(60) Provisional application No. 61/794,240, filed on Mar. 15, 2013.

(51) Int. Cl.
*G01N 1/22* (2006.01)
*G01N 33/00* (2006.01)
*G01N 30/88* (2006.01)
*G01N 1/10* (2006.01)
*G01N 1/20* (2006.01)
*G01N 30/02* (2006.01)

(52) U.S. Cl.
CPC .............. *G01N 2001/2267* (2013.01); *G01N 2030/025* (2013.01); *G01N 2030/8854* (2013.01); *G01N 2030/8886* (2013.01)

(56) References Cited

U.S. PATENT DOCUMENTS

| | | | |
|---|---|---|---|
| 3,842,677 | A | 10/1974 | Bufkin |
| 4,800,763 | A | 1/1989 | Hakkers |
| RE35,874 | E | 8/1998 | Neeser et al. |
| 6,332,349 | B1 | 12/2001 | Poynot |
| 6,865,926 | B2 | 3/2005 | O'Brien et al. |
| 7,162,933 | B2 | 1/2007 | Thompson et al. |
| 7,589,151 | B2 | 9/2009 | Aoki et al. |
| 7,874,221 | B1 | 1/2011 | Mayeaux |
| 8,056,399 | B2 | 11/2011 | Thompson et al. |
| 9,097,695 | B2 | 8/2015 | Kreil |
| 2011/0138877 | A1 | 6/2011 | McCauley et al. |
| 2013/0104597 | A1 | 5/2013 | Rillo Millán et al. |
| 2013/0192339 | A1 | 8/2013 | Kriel et al. |
| 2013/0263680 | A1 | 10/2013 | Barere |
| 2013/0312542 | A1 | 11/2013 | Rolston |
| 2015/0000426 | A1 | 1/2015 | Rolston |

FOREIGN PATENT DOCUMENTS

| | | |
|---|---|---|
| CN | 201716213 U | 1/2011 |
| CN | 102770759 A | 11/2012 |
| EP | 0965831 A1 | 12/1999 |
| EP | 2495517 A1 | 5/2012 |
| JP | 552718 A | 3/1993 |
| JP | 1239289 A | 9/1995 |
| JP | 2000097819 A | 4/2000 |

OTHER PUBLICATIONS

International Application No. PCT/US14/027787, Written Opinion, dated Jul. 24, 2014.
European Search Report, App. No. 14764301.9-1553 dated Oct. 13, 2016.
Singapore Examination Report for cognate filing dated Oct. 4, 2016.
English translation of the First Office Action CN 201480027141.0, dated Jul. 4, 2017.
First Office Action 201480027141.0.
English translation of CN 1482444 A.
English translation of CN 201716213U.
English Abstract of JP 552718.
English Abstract of JP 7239289.
English Abstract of JP 2000097819.
Japanese Patent Office, Application No: 2016-502625 Search Report, dated Oct. 19, 2017 Global Dossier.

COMPOSITE GAS SAMPLING SYSTEM

This application is a divisional application of Ser. No. 14/205,526 filed on Mar. 12, 2014, now U.S. Pat. No. 9,562,833 issued Feb. 7, 2017 and claims priority to U.S. Patent Application Ser. No. 61/794,240 filed Mar. 15, 2013.

FIELD OF INVENTION

This invention relates to collecting composite gas samples for analysis, and particularly for composite sample collection after a cryogenic gas has been conditioned by a system of the type described in U.S. Pat. No. 7,484,404, Thompson, which is owned by the Applicant herein and sold as a Mustang Sampling system. More particularly, this composite sample system is complementary to a gas sample conditioning vaporizer employed to collect conditioned vaporized samples of liquid natural gas and/or natural gas liquid.

BACKGROUND

Liquid natural gas sampling is governed by the standard ISO 8943 and GIIGNL LNG custody transfer handbook. Europe and other areas of the world impose additional requirements such as mandating composite sampling of transferred LNG contents, and particularly, that from tanker ship off-loading. The standard calls for a composite sampling to be collected for the duration of time that a ship is off-loading. The sampled gas stream is transferred to small cylinder sample containers for storage and comparison to continuous online analysis averages.

During transfer processing of a liquid natural gas shipping vehicle, it is desirable to obtain accurate sampling for auditing the energy content of the off-loaded LNG. This can be accomplished using known techniques such as periodic direct sampling from a takeoff vaporizer stream and/or composite sampling. While direct sampling allows for immediate analysis by an appropriate analyzer such as a gas chromatograph, it provides an accurate portrayal of the content of the LNG off-loaded from the vehicle during the entire transfer process only by extrapolating selected accumulated data. Additionally, manual direct sampling can be taken intermittently, for example, at ¼, ½, and ¾ of vessel cargo transfer. Automatic composite sampling is used to obtain particular volumes of vaporized LNG at select periodic intervals during the transfer processing. However, analysis of the typical composite sample content is available only after the transfer processing is complete.

Conventional composite sampling technology for LNG typically takes the form dome or floating piston systems. Dome systems are bladder based and require a fluid (typically water) to isolate the collection dome from the ambient environment and maintain pressure on the collected samples. The resulting extracted composite sample is subsequently transferred from the dome to sample cylinders for analysis and/or storage for later qualitative analysis. Because dome systems rely on fluid/water failure of associated water seals will contaminate the composite sample.

Floating piston samplers are of a more simple construction than dome samplers and avoid the introduction of water/fluid as the seal method, but rely on mechanical seals. Correspondingly, floating piston systems are believed to minimize the introduction of other ambient gases (e.g., oxygen) into the composite natural gas sample. However, floating piston systems include a number movable parts and seals as well as requiring a motive source to pressurize the piston. Not only do such movable parts introduce sources for sample contamination from leakage and the like, but also it is known that such systems employ relatively higher pressures to evacuate the sample chamber during cycling.

SUMMARY OF INVENTION

It is an object of the present invention to provide a novel sample system and methodology for conditioned vaporized, gas during transfer processing.

It is another object of the present invention to overcome the aforementioned problems associated with conventional structures of the prior art.

Another object of the present invention is to provide an expedient to overcome recognized problems with existing sample collection techniques.

A further object of the present invention is to provide greater flexibility in customizing the sampling technique selection and execution for any particular transfer operation.

Still another object of the present invention is selectively provide coincidental fresh gas and composite gas sample sequestration for analysis.

Yet another object of the invention is to provide a convenient, integrated composite gas sample system with a minimum of moving parts.

These and other objects are satisfied by an apparatus for capturing a periodic gas sample following vaporizing and conditioning into a gas phase of a cryogenic liquid hydrocarbon source during transfer processing, comprising: at least a first and a second vaporized sample input lines each incorporating at least a first direct feed line, a second speed loop line, and a third accumulator feed line; each of the first direct feed lines of the first and second vaporized sample input lines being directly connected to a gas analyzer for on-line, real-time, periodic analysis of a non-composite gas sample; each of the speed loop lines being connected to a speed loop having an a pressure regulator, a high pressure pump, a plurality of solenoid controlled valves for controlled filling of a plurality of non-composite sample cylinders for storage of fresh gas samples obtained at specified processing intervals, and a by-pass outlet to a boil-off-gas system; each of the accumulator lines including at least one solenoid controlled valve, said accumulator line for passing a gas sample of a select volume at select time intervals to a pressure regulator, a solenoid controlled valve, and a gas accumulator for receiving multiple periodic select volume gas samples to create a composite gas sample, and a high pressure pump to maintain pressure sufficient in the gas accumulator to prevent dew point drop-out of the gas sample in the accumulator, a valve controlled outlet from the gas accumulator, and a plurality of sample grab cylinders for receiving composite samples from the gas accumulator upon completion of source processing.

Other objects are satisfied by a system for selected sampling cryogenic liquid hydrocarbon source where the liquid hydrocarbon has been vaporized and conditioned by a vaporizer during transfer processing, comprising: a housing; a controller for controlling the gas sampling operation contained within the housing; a vaporized gas port providing a first, a second and a third gas stream feed lines adapted to receive a vaporized gas sample of a select volume at a select time; a gas analyzer connected to said first gas stream feed line; a speed loop connected to said second feed line; a plurality of removable, sample cylinders connected to the speed loop for collection of non-composite fresh samples at select times directly from the vaporizer; an accumulator connected to said third gas stream for receiving a select volume of gas to create a composite sample of vaporized gas; a pump associated with said accumulator to maintain accumulator pressure at a level to prevent dew point drop out of the vaporized gas; a plurality of removable sample grab cylinders for receiving composite vaporized gas samples from the accumulator; and a residual gas removal array for removing residual gas as from the system following transfer processing of the cryogenic liquid hydrocarbon.

Still other objects are satisfied by the method A method for sampling of vaporized gas from a cryogenic liquid hydrocarbon liquid using a gas sample system, comprising the steps of: obtaining a first vaporized gas sample of selected volume and at first select intervals from a vaporizer connected to a cryogenic liquid hydrocarbon repository; passing a select volume of said first vaporized gas sample to a first sample grab cylinder; pumping a second select volume of said vaporized first gas sample to a composite sample accumulator tank under pressure sufficient to prevent dew point dropout; obtaining a second gas sample of selected volume at select interval different from the first select interval; passing a first select volume of said vaporized second gas sample to a second sample grab cylinder; pumping a second select volume of said vaporized second gas sample to the composite sample accumulator tank under pressure sufficient to prevent dew point dropout to obtain a composite gas sample; passing the composite gas sample to a select one of a plurality of removable composite sample collection cylinders for receiving said composite vaporized sample from the accumulator tank; removing the select one of the composite sample cylinders; and removing at least said first sample grab cylinder.

The sample system of the present invention is designed to take timed samples after an sample conditioning system has converted a liquid sample to a gas from one or more input gas streams and provide an associated gas chromatograph or other analyzer with a direct feed for instant analysis, a fresh sample for subsequent analysis at select time intervals during processing and a composite sample for subsequent analysis representative of the entire gas content over the entire sample gathering process. That is, for example, after loading or unloading a ship or container has been completed, the composite sample is in the accumulator, the sampler is turned off. The associated sample cylinders, generally having a 500 cc volume are then filled from the accumulator. After the sample cylinders have been filled, the remaining gas in the accumulator is vented and the system cleaned by use of gas purge, vacuum etc.

For control of the various processes carried out by the invention, use of a resident Programmable Logic Controller (PLC) is preferred. The PLC controls the sequential operations and timing of the composite sample pumps and gas line valves to perform the desired incremental sampling. Furthermore, when redundant or multiple gas streams and pumps are utilized, the invention contemplated that they all feed into a common accumulator rated for the system.

The inventive system does not rely only on volume measurements but also facilitates controlled, periodic sampling based on sample accumulation discrete, known time intervals. That is, the continuous sampling process to fill the sample cylinders provides more accurate results based on its more technical approach to sample collection by relying on select timing of sample accumulation rather than sample gas flow, alone. The invention contemplates a sample system that functions to obtain samples while maintaining relatively low pressures using a static structure (no moving parts) thereby minimizing risks of leakage and contamination. Furthermore, use of the invention substantially reduces the risk of Joule-Thompson cooling and concomitant hydrocarbon dew pint dropout which adversely impacts the accuracy of the samples being analyzed.

For definitional purposes and as used herein "connected" includes physical, whether direct or indirect, affixed or adjustably mounted, as for example, the composite sample system is connected to the a vaporizer, the speed loop line is connected to the sample grab cylinders and the bypass. Thus, unless specified, "connected" is intended to embrace any operationally functional connection.

As used herein "transfer processing" means any processes involving the movement of cryogenic liquid from one place to another in the conventional sense as well as from or to any large cryogenic liquid natural gas container such as ships, railcars or trucks.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawing, and which is shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION OF THE DRAWINGS

Figure 1:
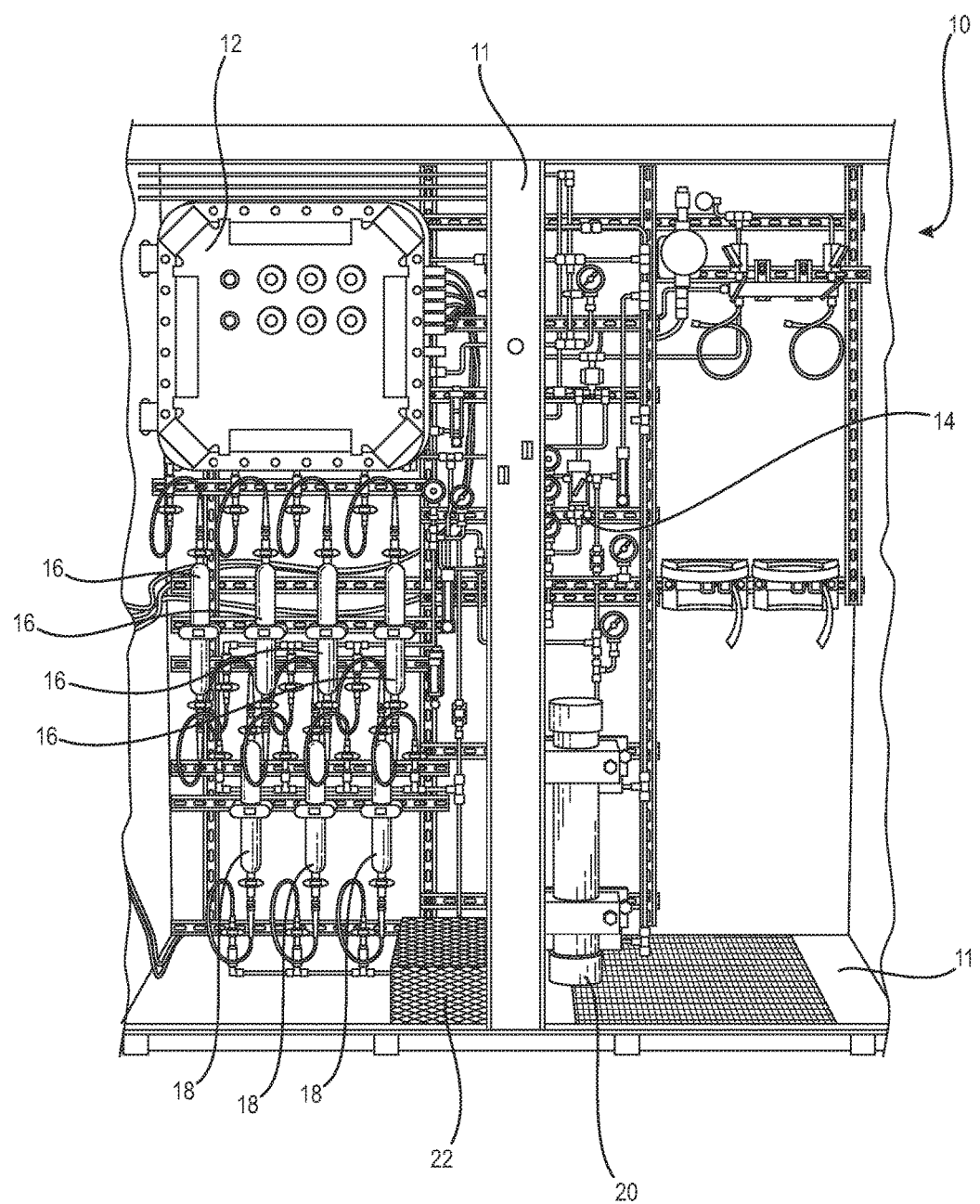
FIG. 1 is a depiction of a composite sample system in accordance with an embodiment of the invention.

The embodiment illustrated in FIG. 1 includes the composite sample system 10 contained in housing 11. The system 10 provides a representative gas composition sample by taking small bite size samples over a period of time. The system 10 includes a programmed logic controller (PLC) 12 with a connection to a remote communication facility for controlling the valves and solenoids and indicator lights for system operation as well as monitoring system status. In addition to the controller 12, the housing 11 of sampling system 10 contains sample pumps 14, a plurality of removable accumulator grab sample cylinders 16 (four cylinders are used in the illustrated system), a plurality of fresh sample cylinders 18 each for receiving a respective gas sample at a specific interval (e.g., ⅓ load transfer, ½ load transfer, and ⅔ load transfer) during the transfer processing. The grab cylinders 16 are connected to accumulator 20 through appropriate tubing for communication the composite sample. The accumulator 20 which receives a multiplicity of samples of a specified small volume, e.g., 0.5 cc, at a preset time interval (i.e., 1 sec.) under conditions (pressure and temperature) maintained to prevent dew point dropout. Similarly when feeding the composite gas from the sample accumulator 20 to the respective grab sample cylinders, the associated pump(s) must maintain the pressure of the gas to prevent dew point drop out. For maintenance of system stability, the interior of cabinet 11 includes the electrical housing heater 22 to maintained temperatures at an elevated level.

In operation, the composite sample system according to the invention grabs a fresh, 0.5 cc, sample every second, storing it in the accumulator 20 for transfer to the associated grab cylinders 16 following the conclusion of the transfer operation. The composite sample can then be removed and transferred to a laboratory or analyzer site for subsequent analysis.

Figure 2:
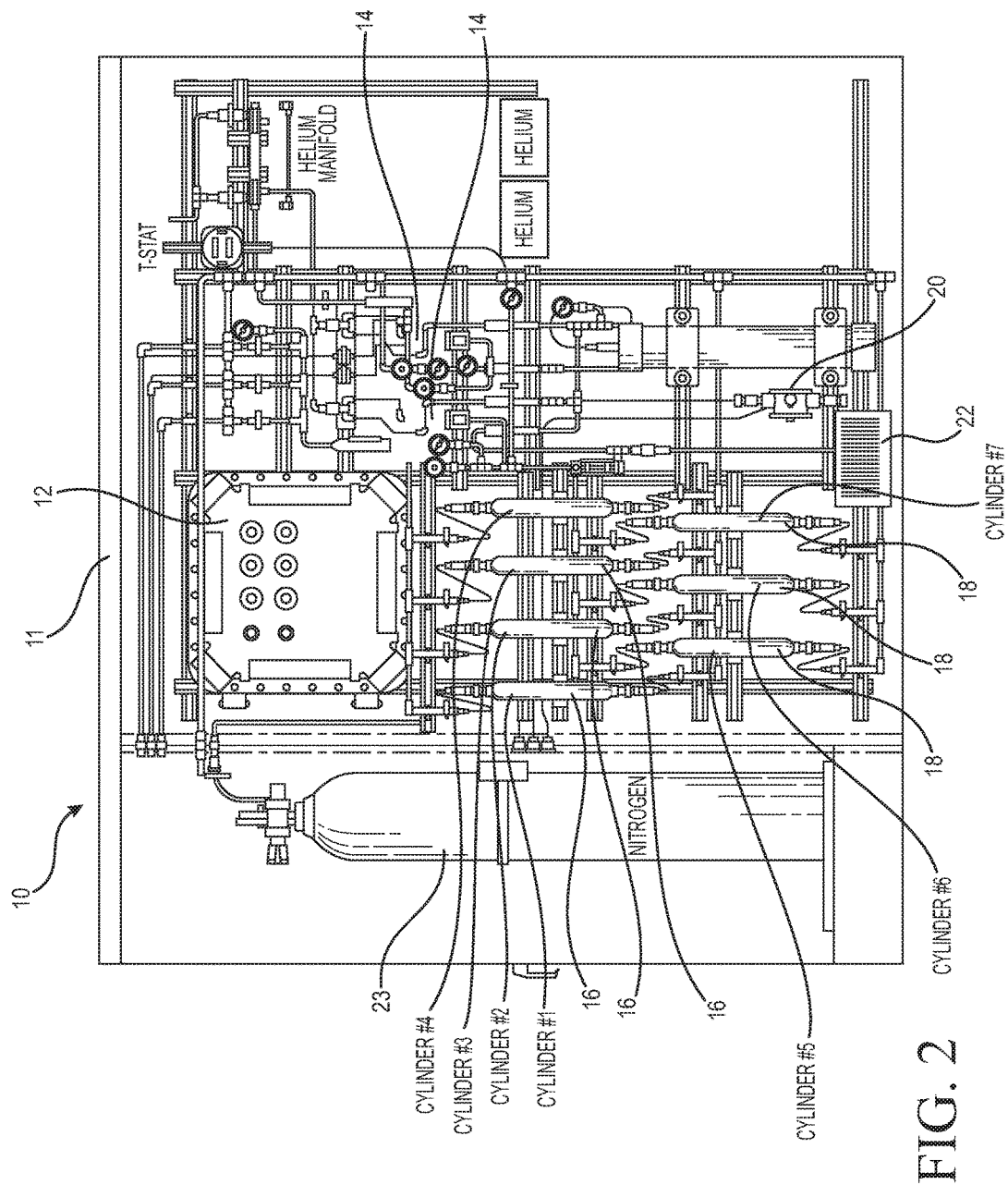
FIG. 2 is a schematic diagram of an embodiment of the invention.

The invention contemplates residual sampled gas removal at the conclusion offloading or transfer processing to reset the system for the next processing operation. FIG. 2 illustrates a gas purge subsystem based on nitrogen gas fed into the system from the tank 24. The purging operation can be completely automated or may be semi-manual (the nitrogen regulator is opened manually when the PLC has been instructed to open the system valves for purging.

Figure 3:
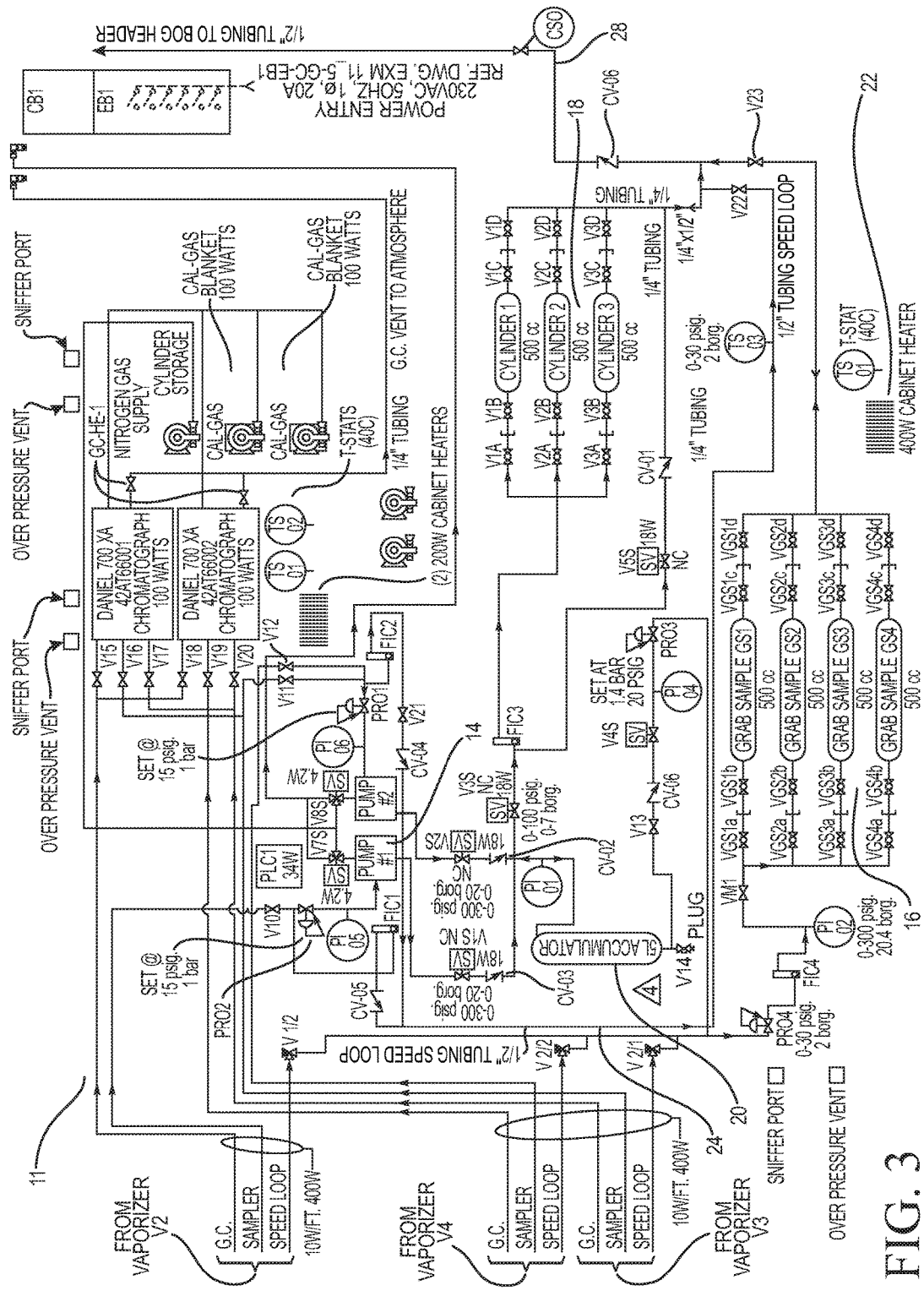
FIG. 3 is a schematic diagram of a multi-stream, multi-sample collection embodiment of the invention.

Turing to the embodiment illustrated in FIG. 3, it illustrates a multipath, multi-vaporizer takeoff system for multiple simultaneous inputs. This embodiment also provides speed loops 24 that provide alternative feed lines for the vaporized gas directly from the vaporizer to one or more select collection cylinders and/or overflow from the gas pumps 14 associated with the accumulator 20. The particular arrangement provides the system user with the greatest flexibility by allowing for either collection cylinder set to be used for non-composite sampling as well as providing venting to line feed 28 for a BOG (boil-off-gas) collector/header system.

Figure 4:
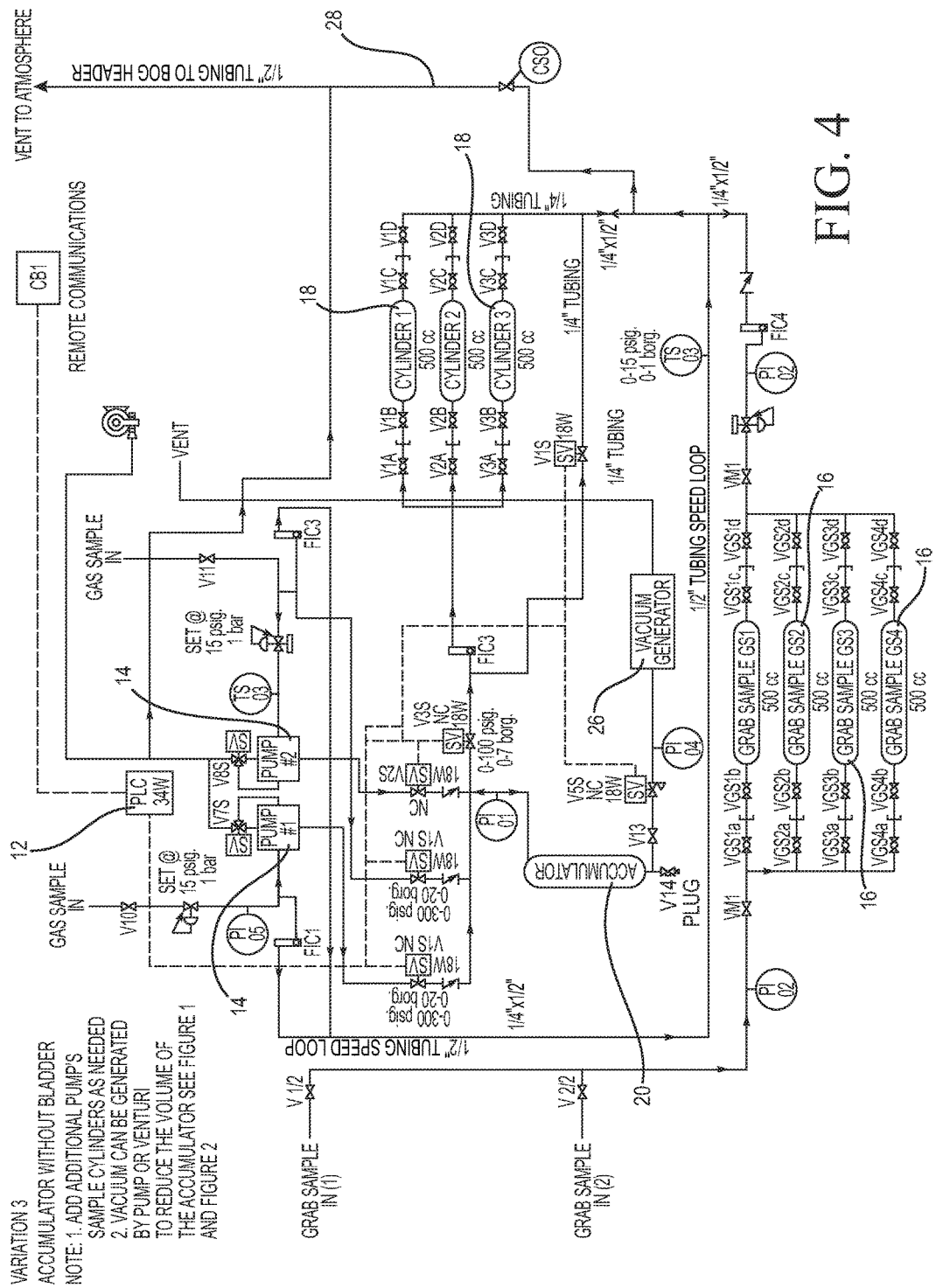
FIG. 4 is a schematic diagram of an embodiment of the invention that with a bladderless accumulator and a vacuum unit for removing residual gas from the system upon completion of a transfer process.

Another option for resetting the system is illustrated in FIG. 4 where a vacuum generating unit 26 is disposed in line with the system and activated by the PLC 12 has all valves opened, to create a negative system pressure and move the residual gas to an appropriate outlet such as a BOG header 28 or using the above-mentioned positive pressure purging gas, e.g., Helium, from the tank 23 to push the residual gas to a vent or the like. Once removed, the system has been effectively reset and is ready for the next sampling operation.

The invention has been disclosed in the forgoing specification. It is understood by those skilled in the art that many modifications and embodiments of the invention will come to mind to which the invention pertains, having benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

We claim:

1. A system for selected sampling cryogenic liquid hydrocarbon source where the liquid hydrocarbon has been vaporized and conditioned by a vaporizer during transfer processing, comprising:
   a housing;
   a controller for controlling the gas sampling operation contained within the housing;
   a vaporized gas port providing a first, a second and a third gas stream feed lines adapted to receive a vaporized gas sample of a select volume at a select time;
   a gas analyzer connected to said first gas stream feed line;
   a speed loop connected to said second feed line;
   a plurality of removable, sample cylinders connected to the speed loop for collection of non-composite fresh samples at select times directly from the vaporizer;
   an accumulator connected to said third gas stream for receiving a select volume of gas to create a composite sample of vaporized gas;
   at least one pump associated with said accumulator to build accumulator pressure at a level to prevent dew point drop out of the vaporized gas;
   a plurality of removable sample grab cylinders for receiving composite vaporized gas samples from the accumulator;
   a residual gas removal array for removing residual gas as from the system following transfer processing of the cryogenic liquid hydrocarbon.

2. The system of claim 1 further comprising a redundant vaporized gas port connected to the accumulator.

3. A method for sampling of vaporized gas from a cryogenic liquid hydrocarbon liquid using a gas sample system, comprising the steps of:
   obtaining a first vaporized gas sample of selected volume and at first select intervals from a vaporizer connected to a cryogenic liquid hydrocarbon repository;
   passing a select volume of said first vaporized gas sample to a first sample grab cylinder;
   pumping a second select volume of said vaporized first gas sample to a composite sample accumulator tank under pressure sufficient to prevent dew point dropout;
   obtaining a second gas sample of selected volume at select interval different from the first select interval;
   passing a first select volume of said vaporized second gas sample to a second sample grab cylinder;
   pumping a second select volume of said vaporized second gas sample to the composite sample accumulator tank under pressure sufficient to prevent dew point dropout to obtain a composite gas sample;
   passing the composite gas sample to a select one of a plurality of removable composite sample collection cylinders for receiving said composite vaporized sample from the accumulator tank;
   removing the select one of the composite sample cylinders; and removing at least said first sample grab cylinder.

4. The method of claim 3 further comprising the step of removing residual gas from the gas sample system after removing the composite sample cylinder and the sample grab cylinder.

5. The method of claim 3 further comprising the step of purging residual gas in the gas sample system after removing the composite sample cylinder and the sample grab cylinder.

6. The method of claim 3 further comprising the step of analyzing the content of the removed composite sample cylinder and said sample grab cylinder.

* * * * *